United States Patent [19]

Riley

[11] Patent Number: 4,966,841

[45] Date of Patent: Oct. 30, 1990

[54] ENHANCED VECTOR PRODUCTION AND EXPRESSION OF RECOMBINANT DNA PRODUCTS

[75] Inventor: Donald E. Riley, Seattle, Wash.

[73] Assignee: The Board of Regents of the University of Washington, Seattle, Wash.

[21] Appl. No.: 53,390

[22] Filed: May 22, 1987

[51] Int. Cl.[5] .................. C12P 21/00; C12P 19/34; C12N 15/00; C07H 15/12

[52] U.S. Cl. .................. 435/69.1; 435/91; 435/172.3; 435/320; 536/27

[58] Field of Search .................. 435/68, 70, 320, 91, 435/172.3; 536/27

[56] References Cited

U.S. PATENT DOCUMENTS

| | | |
|---|---|---|
| 3,923,603 | 12/1975 | Chakrabarty et al. . |
| 4,262,090 | 4/1981 | Colby, Jr. et al. . |
| 4,374,927 | 2/1983 | Sninsky et al. . |
| 4,497,796 | 2/1985 | Salser et al. . |
| 4,499,188 | 2/1985 | Konrad et al. . |
| 4,510,245 | 4/1985 | Cousens et al. . |
| 4,562,155 | 12/1985 | Ricciardi et al. . |
| 4,590,159 | 5/1986 | Markovitz et al. . |
| 4,590,162 | 5/1986 | Grinter . |
| 4,615,974 | 10/1986 | Kingsman et al. . |
| 4,634,678 | 1/1987 | Salstrom et al. . |
| 4,663,281 | 5/1987 | Gillies et al. .................. 435/68 |

FOREIGN PATENT DOCUMENTS

| | | |
|---|---|---|
| 0096586 | 6/1983 | European Pat. Off. . |
| 0121386 | 3/1984 | European Pat. Off. . |
| 0131843 | 7/1984 | European Pat. Off. . |

OTHER PUBLICATIONS

Riley et al., 1986 Xrep, a plasmid-stimulating X chromosoaml sequence bearing similarities to the BK virus replication origin and viral enhancers, Nucleic Acids Research 14, 9407–9423.

Hamada, H. 1986 Random isolation of gene activator elements from the human genome. Mol. Cell. Biol. 6, 4185–4194.

Conrad et al., "Isolation and Characterization of Human DNA Fragments with Nucleotide Sequence Homologies with the Simian Virus 40 Regulatory Region," *Molecular and Cellular Biology*, Aug. 1982, pp. 949–965.

Gorman et al., "Recombinant Genomes Which Express Chloramphenicol Acetyltransferase in Mammalian Cells," *Molecular and Cellular Biology*, Sep. 1982, pp. 1044–1051.

Gorman et al., "High Efficiency DNA-Mediated Transformation of Primate Cells," *Science*, vol. 221, Aug. 1983, pp. 551–553.

Gruss et al., "Simian virus 40 tandem repeated sequences as an element of the early promoter," *Proc. Natl. Acad. Sci. U.S.A.*, vol. 78, No. 2, pp. 943–947, Feb. 1981.

Herbomel et al., "Two Distinct Enhancers with Different Cell Specificities Coexist in the Regulatory Region of Polyoma," *Cell*, vol. 39, 653–662, Dec. 1984 (Part 2).

McCutchan et al., "DNA sequences similar to those around the simian virus 40 origin of replication are present in the monkey genome," *Proc. Natl. Acad. Sci. U.S.A.*, vol. 78, No. 1, pp. 95–99, Jan. 1981.

Rosenthal et al., "BK Viral Enhancer Element and a Human Cellular Homolog," *Science*, vol. 222, 18 Nov. 1983, pp. 749–755.

Soeda et al., "Sequence from Early Region of Polyoma Virus DNA Containing Viral Replication Origin and Encoding Small, Middle and (Part of) Large T Antigens," *Cell*, vol. 17, 357–370, Jun. 1979.

Stillman et al., "T Antigen and Template Requirements for SV40 DNA Replication in Vitro," *The EMBO Journal*, vol. 4, No. 11, pp. 2933–2939, 1985.

Yang et al., "BK Virus DNA: Complete Nucleotide Sequence of a Human Tumor Virus," *Science*, Oct. 1979, pp. 456–462.

*Primary Examiner*—Charles F. Warren
*Assistant Examiner*—Christopher S. F. Low
*Attorney, Agent, or Firm*—Christensen, O'Connor, Johnson & Kindness

[57] ABSTRACT

A 2,356 base pair fragment isolated from the human X chromosome, designated as Xrep, has been found to exert a positive effect on plasmid replication in both prokaryotic and eukaryotic cells. The Xrep, in addition, has been found to increase transcription of DNA, thus leading to increased expression of desired protein products. The Xrep segment has been fully sequenced and portions thereof have been found to exhibit homologies with enhancer sequences contained in various viruses.

14 Claims, 12 Drawing Sheets

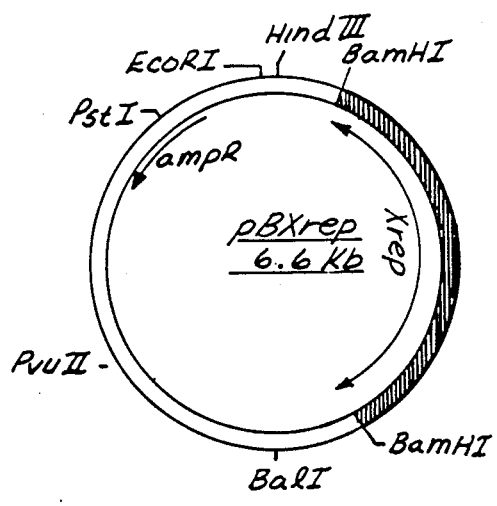
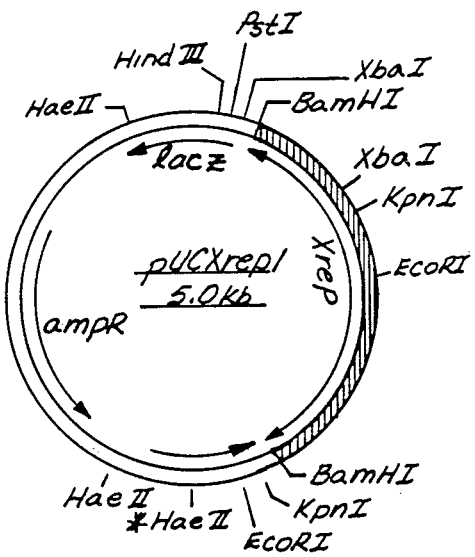
Fig. 1.
Fig. 2.
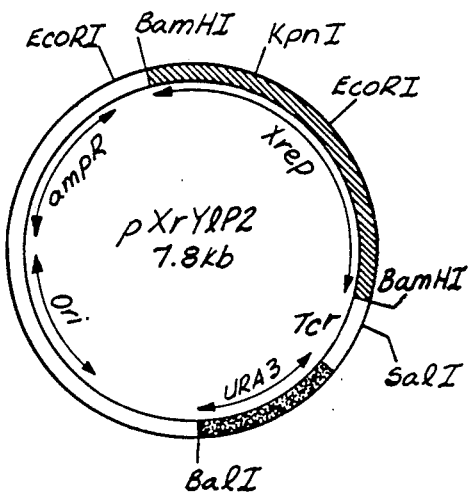
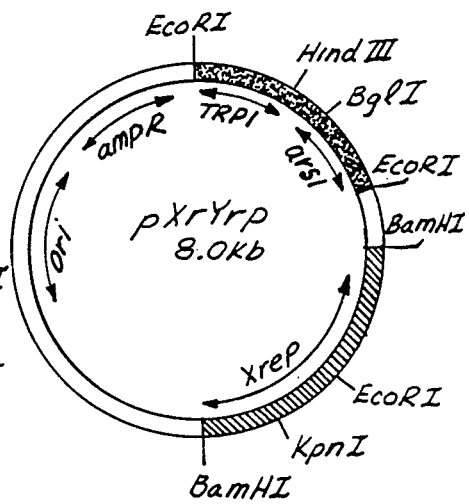
Fig. 3.
Fig. 4.

```
    ELS          BamHI
α→  ↓            ↓
GGATCCAGTG CCAGACAGCT GTATGAACAC GCTCTCCTGG CTACCTGGGC CCCATCTGTT    60
    ↑BamHI
TGCTTCGGGC TGACAGTGAG ATAAGGGACA ATGACTTTC  CCTCCTGAGC CACATGTTAG   120

TGAAGCGGTG GAGATAATTC TGCTCTGAGT CCTGACGGGA AGTTGCTGGG GAGCAACTTT   180

ACAGTGCTCC TGGCTTGGGG CACTACCCAC TCGGGCTTT  GTGGCAAGCT ATTCCCCCTC   240
                                       TRUE PALINDROME
ACGGCCAAGG AACCTGGCTT CCCATA|CCAC CTCCTTTCCT CCACC|ACCG TCTCCCTATC   300

TGAATCCTAT TCACTTTTCA GGTCTTGGCT CAAATCCTGA CTCCCTGTGA AGATGTCCTG   360
                                                    2
ACCCTCCCAG CCTAGAGCCA CTACTCCCTC CTTGAATCTC AGGATCTCCA ACTGTGACAT   420
           1                                  ┌─────┐
GGCCATA|CTA TTTGCCACA|T CCCCACAGAC GGATTGTGAT G|AGGAAG|GAA AGAGAGAGTC   480
                                                        3
                                              ┌────┐
CATGTAGCAT GCTAGATGCG CTCTGACCCC CAGCATGCAG GCATGGGCGG CTTGATCACG TGCCT|CTTCC|   540
        4                       XbaI
|CTTCCT|CCC CTTGGGGAT CATTCTGTG CTAGTTGTCC CCTCAGTTGC AATGTCACAG   600
TCTAGATAAT
                           5       ELS  KpnI
ACCATGGGGC CACACATCTCAT C|TTCCT|CAC CTTCCAGCAT CCAGCATACA ATAAACACCA   720

TCGTAACCAT TTTTCATTGG GCATCTTAGG|GTACCATGTG GCAGGCACTC GGCTGTGTAG   780
```

Fig. 5A.

```
GTAATGCACA CAAGTGTAGT CCTCACTCAT TCCCCTCCTA GCTCTCTTCC AGGATGTGCA   840
GGCATTGATT CTCCTTTGAG TTATATCAGA CAGATTGTGT CAACCGCTAC CAAGGTCGCA   900
                                            α
                                           ↓
TCATGAGTAA GTAGCCCTGA CAGGCATCAA GTACTATGCT AGATTAAGTT TCTAATGAAT   960
GCCTGCGAAA GGGTGGTTGG CAGGAGGGAC AGATGTAGAG CCCAGAGTAC GACTGCCTGC  1020
CCCGTGCTTT TACCCGGCAG AGGCAGGCCT GCTTGAGAGA AAGCTGTACG CAATAAAGAC  1080
ATAGGATTCA GCGGGTCCTC GAGCTTAGGA AAGGGGATAT AGTCGCTCCA GGACAGGGGG  1140
AGAAATGGAG AGGGGATGAG TCACGCTAAA CCTCAAGGCA ACTGTCCCAG GGAATTCCCC  1200
ACTTACTGGG CCTTTCGCAG GCCAGGCAGG CTAGGCACAA AGCAACCTGA AGCTACCTTC  1260
ACCCTGAGGG CATCCACTCG GACCCTAGGT CATTGCTGTG GCTTGAGAGT TAAAGATGTG  1320
ACTACCCTGC TCCCCACCCC CACAACATCC AAGCCCATCA GTAAATGAGT AAGTGGTTCA  1380
TCTACACACA CACACACACA CACACACACA CACACACACA GCCAGAAGCG CACTCTGGCG  1440
TGCACACACA TGAGACTGAC CTCACTTGGG TACATTCATC TAGTCACACA CATTCACACC  1500
CACACTCTGA CCCACACCAT CATCCATGCA AACCCTCACA CACTTAAACA CATCCCCTCC  1560
```

*Fig. 5B.*

```
CCAGAACCAA ATTTGACCTA ACATGGCTGA TGGGGCGTGG GAGGGTCCAG TCAGGATGTC 1620
CCCTCTGGAC CTGGCCCACT CACCGACCTG TGAACTCCAG GCCCCTTGCT CAAGGTGGAG 1680
CCCCCACCTG TCCCTGTCCT AGTGGTCACA GGTCCTGAAC ACCCCACTC TCGGCCCCCG 1740
AAGCCTGGTC ACCATCGCGT GCACAGAATC CTGGGAGCCT GGCTGGCCTT AGGGTAGGGG 1800
GTATGGGAAA AGGGAAAGAT GTGGGGCATA GTGCCCTGCC CTGCTCAGCC GCCTCCTCCC 1860
TCGGGATTTT CCATCCCGGC TCGCGCGGGC CCGCTAGAAG CCGGTGCGCT TTGTCTCCCG 1920
                       MspI                MspI
CCCCGCTCCT GGCACGTTTC CGTGGAAGCT GCCCGCGCCG GCCGAAGCC CCCCCTCCGC 1980
                                          B
GGCCGCGCCC CCCGCCCAGC CCGCGGGCGC AGCCCCATGC TGCCGGCGACC GCCGCTTTGT 2040
CCTCTCGAGG ATGCCTGGGC CGAGCGCGAA AGCCCCATGC TTGGGTGCGC CCTGCATCGG ACGGAGCAGC 2100
GTCCTGGAAG CAGGTCCCCG AGCCTCGGTT TGGGTGCGC GTAGCGTCTA CCTGGAGCTC TTGAGTGCTT 2220
                                                                PvuII
CCCCAAAGAT TCGCGGGCAC AAGGTTGGGG GTAGCGTCTA ACATGCCCAT CTGGGATTGG CCCCAGCTGC 2280
         B
GAGGGGGAGA CCCGCCCCGT CCCGCTCTGT ACATGCCCAT CTGGGATTGG CCCCAGCTGC 2280
GGTGCCAGAG GCTCGGTCCC CGGGGCGTGG TGGGCTAGGG CGGGTCGTCT TGACTTAGAG 2340
         BamHI
CCCCAGGCCT GGATCC                                                  2356
```

*Fig. 5C.*

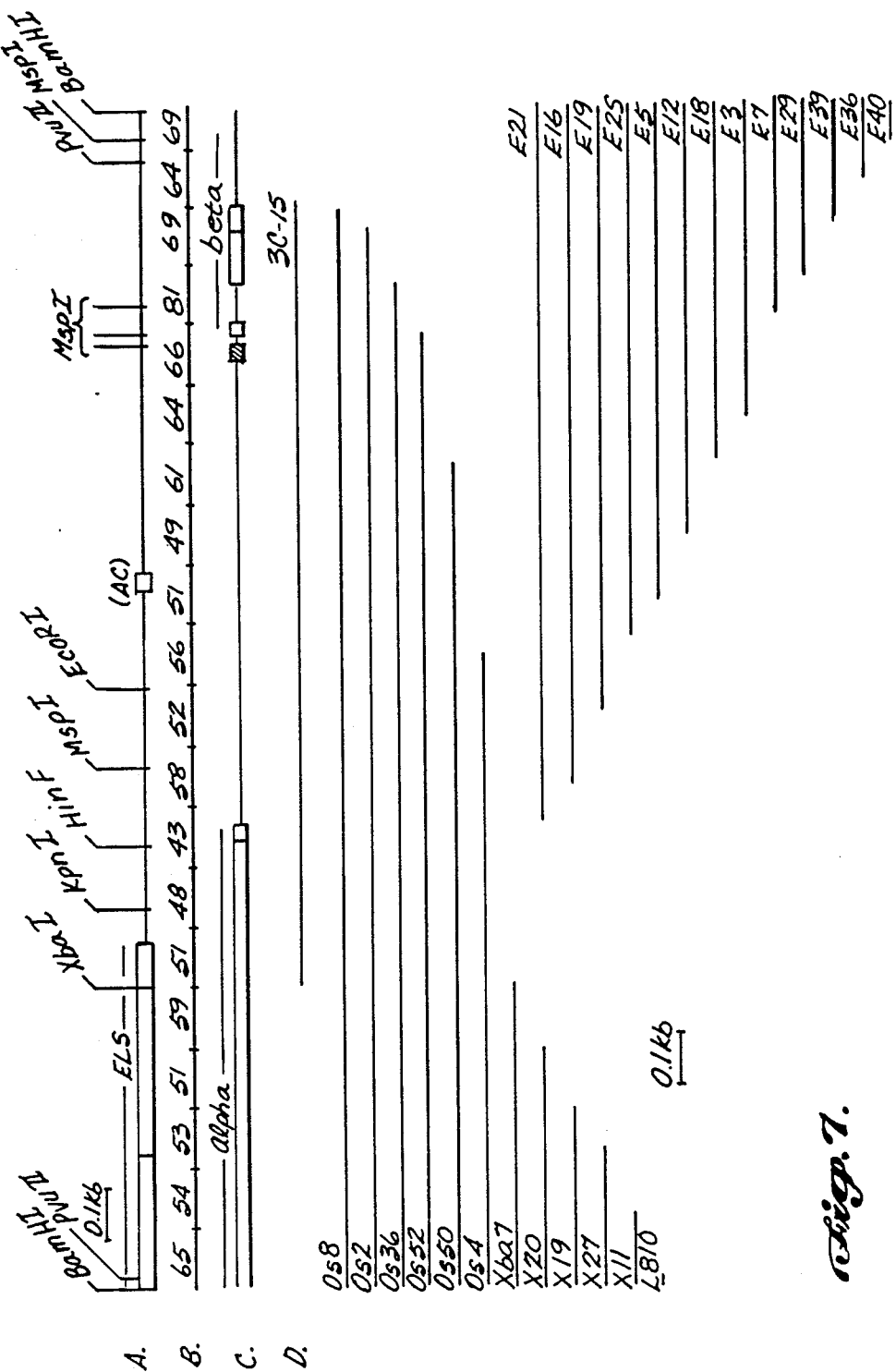

Py    CCTC(C/T)₁₀CCTC
BK    CCTC(G)₈CCTC
SV40  CCTCC(A)₆CCTC
                G
Xrep  CCA CCTCC(T)₃CCTCC ACC

*fig. 8A.*

A  C
ENHANCERS(3)—TRUE PALINDROME—20bp—GAATCCTATTCTTTT—EARLY VIRAL GENES

AC
—Orf—TRUE PALINDROME—20bp—GAATCCTATTCTTTT—ENHANCERS(3)

*fig. 8B.*

ENHANCED VECTOR PRODUCTION AND EXPRESSION OF RECOMBINANT DNA PRODUCTS

TECHNICAL FIELD

The present invention relates to recombinant DNA materials and methods and, more particularly, to a nucleotide sequence or fragment capable of providing both increased levels of cloning and expression vectors in both prokaryotes and eukaryotes and also enhanced transcription of genes in eukaryotic host cells. This plasmid growth enhancing nucleotide sequence is derived from the human X chromosome.

BACKGROUND OF THE INVENTION

Proteinaceous molecules, such as enzymes, hormones, storage proteins, binding proteins and transport proteins may be produced by recombinant DNA techniques. For instance, DNA fragments coding for selected proteins, together with promoter sequences are ligated to an appropriate vector in the presence of ligating enzymes. The recombinant vector is inserted within host prokaryotic or eukaryotic cells. Transformed host cells are identified, isolated and then cultivated to achieve multiple copies (replication) of the recombinant DNA vector and/or expression of the protein or polypeptides coded for by the foreign DNA.

To enable the foregoing procedures to be used as a viable method of producing proteinaceous products on a commercial scale, intense efforts are being made to increase the efficiency of such procedures to achieve higher output levels of recombinant DNA products. One possible technique for increasing the yield of such products is by identifying and employing more highly efficient promoters. As used herein, the term "promoter" refers to a DNA segment capable of functioning to initiate transcription of an adjoining DNA segment. Transcription is the synthesis of messenger RNA ("mRNA") complementary to one strand of the DNA adjoining the promoter region. In prokaryotic host cells, mRNA synthesis is catalyzed by RNA polymerase, which is the same enzyme employed in ribosomal RNA ("rRNA") synthesis and transfer RNA ("tRNA") synthesis. In eukaryotic cells, the synthesis of the three forms of RNA are catalyzed by distinct polymerases with eukaryotic mRNA syntheses catalyzed by RNA polymerase II.

The promoter provides the binding site for RNA polymerase or RNA polymerase II so that the proper strand of DNA serves as a template for mRNA synthesis. The promoter also regulates the rate at which transcription occurs. Some promoters are more accurate than others and/or regulate the synthesis of much larger quantities of mRNA than produced by less active promoters. As such, protein expression is enhanced by selecting efficient promoters compatible with the host cells. An example of an efficient promoter for plasmid vectors effective in *Escherichia coli* ("*E. coli*") host cells is the promoter from the lac operon. Efficient promoters for protein expression in yeast cells include the promoters for alcohol dehydrogenase ("ADH") or the alpha-factor gene, Kurjan and Herskowitz (1982) *Cell,* 30:933–943. Examples of the use of promoters in yeast vectors from the gene coding for phosphoglyceride kinase are set forth in U.S. Pat. No. 4,615,974.

For the cloning of genes and the production of desired products in eukaryotic hosts, viral vectors are commonly employed, for instance from the simian virus 40 ("SV40"), polyoma, human BK virus ("BK") and adeno viruses. These virions include strong promoters. The viral vectors are used in their "natural" form and also in mutated form. Moreover, not uncommonly, the promoter region of the viral DNA is utilized in nonviral derived vectors, such as vectors originating from the pBR322 *E. coli* bacterial plasmid. Examples of nonviral derived vectors utilizing viral promoter regions are disclosed in U.S. Pat. Nos. 4,510,245 and 4,562,155.

In addition to employing promoters in their "natural" state, attempts have been made to increase vector replication and expression of protein products by development of mutated promoters. An example of such a promoter is disclosed in U.S. Pat. No. 4,374,927.

In addition to promoters, transcription of DNA in viral hosts is facilitated by enhancers. Enhancer sequences have been found in the DNA of several viruses of higher eukaryotes, including the SV40, virus murine leukemia virus, polyoma virus, bovine papilloma virus and BK virus. The enhancer sequences typically greatly increase the transcription of the gene from virtually any nearby promoter. They may be located great distances upstream or downstream from the gene. It is not known how the enhancer sequences exert their effect. One theory is that enhancer sequences maintain the DNA in an open, protein-free confirmation, thus providing entry sites for RNA polymerase. Except for a "consensus sequence" of from about seven to ten base pairs that have been found in a number of enhancers, there seems to be little homology among the various viral enhancers which have been identified.

The use of enhancers to increase transcription of DNA has been described in the literature. For example, Rosenthal et al. (1983) *Science,* 222: 749–754, describes the use of the BK viral enhancer to increase transcription. Also, the enhancer sequences from SV40 are commonly employed in cloning and expression vectors. See, for instance, Old and Primrose, *Principles of Gene Manipulation,* 2nd Ed. pp. 121 et seq., 1981.

SUMMARY OF THE INVENTION

The present invention relates to nucleotide segments derived from the human X chromosome that are capable of increasing the yield of cloning and expression vectors compatible with both prokaryotic and eukaryotic cells. When inserted within expression vectors, including plasmids and cosmids, the human X chromosome derived segments are capable of producing increased yields of the plasmids as well as enhanced transcription of genes in eukaryotes. The increased plasmid production and/or increased transcription leads to higher expression levels of protein products encoded by the genes.

One such X chromosome segment is designated as ("Xrep"). Xrep has been characterized and its nucleic acid sequence determined. Two regions of Xrep, designated as alpha and beta, are important in the plasmid yield increases seen in prokaryotic cells. These regions are located on the opposite ends of the Xrep segment and are separated by approximately 1000 base pairs ("bp"). The beta region by itself has a positive effective on plasmid yield, whereas the alpha region by itself does not. However, the positive effect of the beta region is amplified by about two to three fold by the presence of the alpha region. The alpha region contains a region of approximately 750 bp, designated as ELS, which exhibits close homologies to several known viral enhancers, including the Ela enhancer core found in viral DNA. The ELS region also includes sequences that resemble the enhancer core sequence of SV40. The ELS region further includes a 19 base pair true palindrome which bears similarity to true palindromes located near the replication origins of SV40, BK and polyoma viruses.

In expression studies using the gene coding for the enzyme chloramphenicol acetyltransferase ("CAT") the Xrep segment was found to be capable of increasing expression of this enzyme to levels obtainable using high level promoters and enhancers. The Xrep segment is not simply an alternative promoter in that it will increase expression levels when used in conjunction with strong promoters and it acts over several kilobase distances.

The present invention contemplates the use of the X chromosome derived segments, including Xrep, in the construction of plasmids for high level production of the plasmids in appropriate hosts and also the construction of expression vectors consisting of plasmids or other vectors for increased transcription of genes and, thus, increased expression of gene products. In a further aspect, the present invention also concerns hosts transformed by the plasmids and vectors containing the X chromosome derived segments, including the Xrep segment. The present invention in addition involves a method of producing increased levels of desired protein products by recombinant DNA techniques by utilizing the X chromosome derived segments, including the Xrep segment, in prokaryotic and eukaryotic host-vector systems, and the growing of the host-vector systems, under conditions permitting production of the desired peptide and subsequent recovery of the desired peptide.

In the remainder of the present application and in the claims, the terms "enhance" or "enhancer" when used in conjunction with the Xrep segment or a portion thereof, or similar segment, shall not be limited to the characteristics and activities of known viral enhancers, but may encompass generally DNA sequences capable of providing increased replication of cloning and expression vectors in addition to increased and/or more efficient transcription of genes and a resulting increased expression of polypeptides and proteins encoded by such genes in both prokaryotic and eukaryotic host cells.

BRIEF DESCRIPTION OF THE DRAWINGS

The details of typical embodiments of the present invention will be described in connection with the accompanying drawings in which:

FIG. 1 schematically illustrates the recombinant plasmid pBXrep (formerly designated BamR1) with the Xrep fragment inserted therein, for use in transforming *E. coli* host cells;

FIG. 2 schematically depicts the pUCXrep1 plasmid also containing the Xrep fragment and used in transforming *E. coli* host cells;

FIG. 3 schematically illustrates the shuttle vector pXrYIP2 with the Xrep fragment inserted therein, for use in transforming bacterial or yeast host cells;

FIG. 4 schematically illustrates the shuttle vector pXrYrp with the Xrep fragment inserted therein, for use in transforming bacterial yeast host cells;

FIGS. 5A, 5B and 5C collectively illustrate the nucleic acid sequence for the Xrep segment together with the restriction enzyme cleavage sites being specified;

FIG. 7 contains a restriction enzyme cleavage map of the Xrep fragment and the various mutants thereof shown in FIGS. 6A and 6B;

FIG. 8A illustrates the homology between a 19 base pair palindrome contained in the Xrep segment with similar palindromes found in the polyoma, BK and SV40 viruses;

FIG. 8B consists of a schematic comparison of Xrep sequences with the BK virus replication origin;

Figure 10:
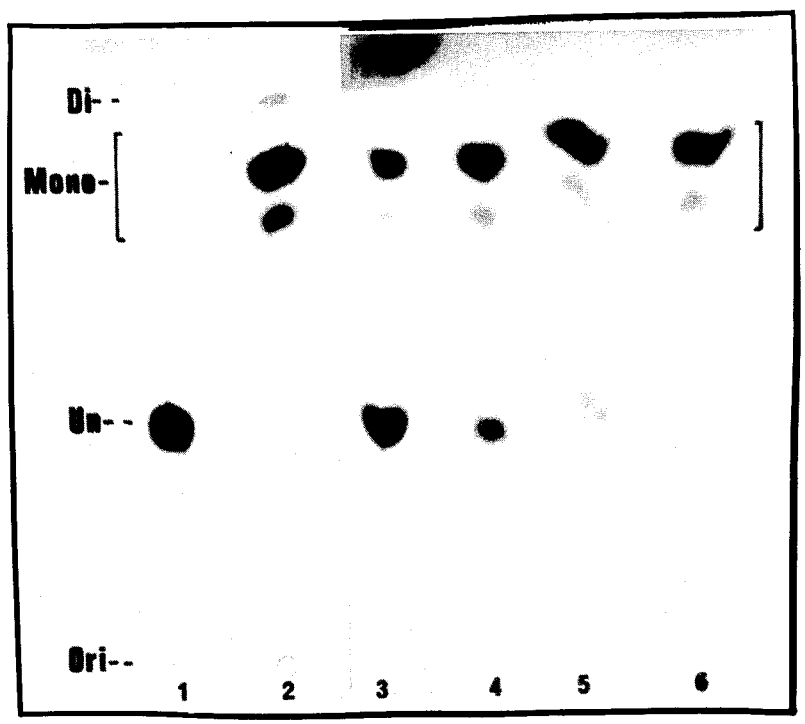
Figure 11:
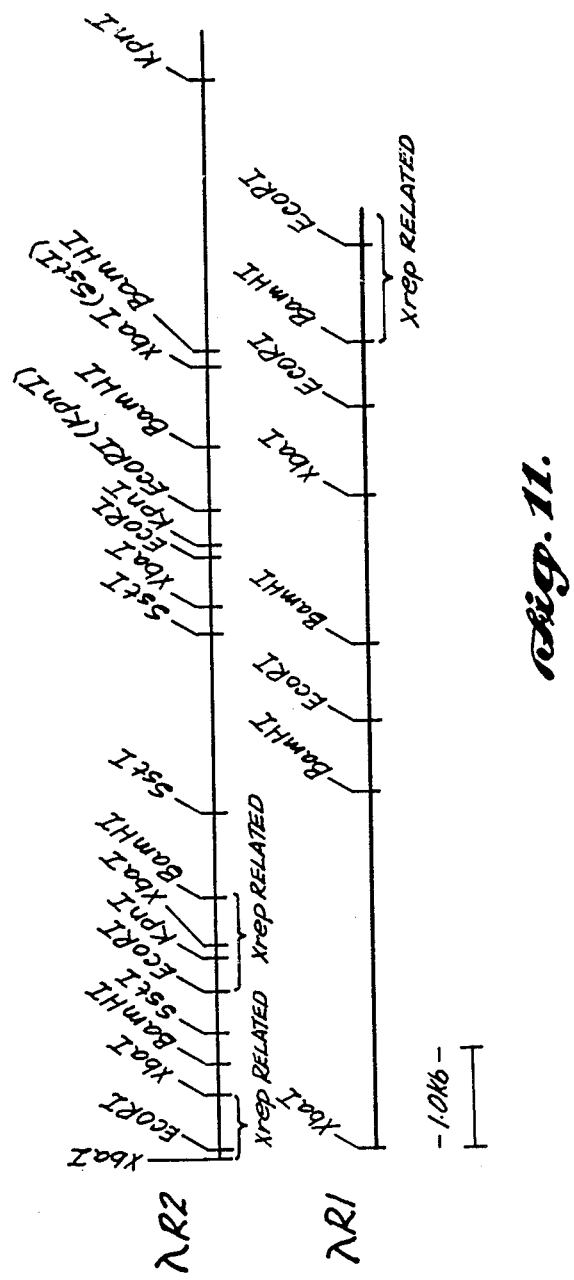

VIGS. 9A, 9B, 9C, 9D and 9E illustrate the strategy employed to construct expression vectors containing the Xrep segment or the ELS fragment thereof at locations both 5' and 3' of a gene encoding a protein production of interest;

FIG. 10 shows an autoradiograph of extracts of mammalian cells transfected with a vector containing the Xrep segment and a gene of interest; and FIG. 11 depicts restriction enzyme cleavage maps of phage clones λ R1 AND λ R2.

DESCRIPTION OF THE INVENTION

Isolation and Cloning of Growth Enhancing Fragments

The enhancer fragment of the present invention is derived from the human X chromosome and, in particular, from the human X chromosome of a lymphoblast cell line, and more particularly the human lymphoblast cell line GM1416. This cell line contains four X chromosomes per cell as is verifiable by cytological Barr body analysis.

The X chromosomes together with the nuclei are isolated from the GM1416 cells by standard technique, for instance, by gently lysing the cell to leave the nucleus intact. The nucleus can be removed from the other cell components by low speed centrifugation, lysed and then the DNA purified from the RNA and proteins of the nuclei.

The recovered, purified genomic DNA is digested with one or more restriction enzymes by standard procedures, such as set forth in Maniatis et al., *Molecular Cloning-A Laboratory Manual* (1982) Cold Spring Harbor Laboratory, Cold Spring Harbor, N.Y. p. 104 et seq. Thereafter, the genomic DNA fragments are separated by size, for instance by electrophoresis on an agarose gel. The DNA fragments within the size range of interest are then cloned. For example, in the present invention, chromosonal DNA fragments in the size range of 1.9 to 2.3 kilobase ("kb") were employed.

To carry out the present invention, various cloning vectors may be used. The vector may be composed of a plasmid, a bacteriophage or a cosmid for transformation of a prokaryotic host. If cloning takes place in mammalian or plant cells, viruses also can be used as vectors.

If a plasmid is employed, it may be obtained from a natural source or artifically synthesized. The particular plasmid chosen should be compatible with the cells serving as the host, whether a bacteria such as *E. coli*, yeast or other unicellular microorganism. The plasmid chosen should have convenient restriction enzyme cleavage sites to cleave the plasmid for subsequent ligation with the X chromosome fragments without causing further digestion of the fragments. To this end, it would be helpful for the plasmid to have single substrate sites for a large number of restriction endonucleases. However, the choice of plasmids is not limited to plasmids containing convenient restriction sites.

Moreover, the plasmid should have a phenotypic property that will enable the transformed host cells to be readily identified and separated from cells which do not undergo transformation. Such a phenotypic selection gene can include genes providing resistance to a growth inhibiting substance, such as an antibiotic. Plasmids are now widely available that include genes resistant to various antibiotics, such as tetracycline, streptomycin, sulfa drugs, penicillin, kanamycin, G478 and ampicillin. When host cells are grown in a medium containing one of these antibiotics, only transformants having the appropriate antibiotic resistant gene will survive.

Rather than utilizing a gene resistant to a growth inhibiting compound to identify transformed host cells, phenotypic selection genes also can include those that provide an essential amino acid or nutrient to permit transformed cells to propagate in a medium which lacks the essential amino acid or nutrient. For instance, for yeast auxotrophs, such nutrients include tryptophan or leucine.

If *E. coli* is employed as the host cell, many possible cloning plasmids are commercially available which may be used in conjunction with the present invention. Preferred plasmids for performing the present invention include, for instance, the pUC series vectors, pNO1523, pKO-1, pNEO, terminator selection vectors like pKK626-7 and pKK65-10, promoter selection vectors like pKK175-6 and pKK232-8, pFB plasmids, pTZ18R, pTZ19R, dual promoter plasmids like pSPT18 and 19, in vitro transcription vectors pSP68 and 69, pUCf1, mammalian expression and shuttle vectors pSVL, pCH110 and pKSV-10, pKK223-3. Any plasmid bearing a pBR type replication origin, $SV_{40}$ replication origin, or yeast or mammalian autonomously replicating sequence (ARS) may be used. Many future plasmid constructs based on the above replication origins, ARS's and promoters (in the case of expression vectors) may be used. Almost all of the foregoing plasmids, including the pBR322 plasmid, are widely commercially available and have been fully sequenced. The sequence of the pBR322 plasmids is set forth in Sutcliff (1979), *Cold Spring Harbor Symp. Quant. Biol.*, 43:77. A significant advantage of this plasmid is that it has seven known unique restriction enzyme cleavage sites at which a plasmid may be cleaved by a specific restriction enzyme, including the BamH I site.

If a bacteriophage is used instead of a plasmid, such phages should have substantially the same characteristics noted above for selection of plasmids. This includes the existence of a phenotypic marker and ligatable termini for attachment of the Xrep (or related) DNA sequences.

To prepare the Xrep-plasmid construct, Xrep and the plasmid are digested with appropriate restriction enzymes and ligated and then the recombinants isolated by standard molecular biological methods. See Maniatis et al., supra at page 8.

If yeast cells are employed as transformants, preferable plasmids include YIP5 and YRp7' as well as other ARS containing plasmids. The YIP5 plasmid is commonly used as a test vector for ARS in yeast while the YRp7' plasmid already exhibits ARS activity.

Certain restriction enzymes (i.e., Pvu II, Bal I) may result in the formation of square or blunt ends. The blunt ends of the plasmid may be joined to the genomic DNA fragments with an appropriate ligase. Alternatively, nucleic acids can be added to the 5' or 3' ends of the plasmid to form cohesive termini, for instance, by use of linker molecules. Cohesive termini may also be formed by removing nucleic acids from the flush ends of the plasmid and genomic DNA fragments with appropriate enzymes. The methods and materials for carrying out these procedures are well known in the art. See, for instance, Maniatis et al., supra beginning at page 390; and Old and Primrose, supra, beginning at page 12.

The recombinant DNA plasmids, as prepared above, are used to transform host cells. The host may be any appropriate prokaryotic or eukaryotic cell. For example, the host may be composed of a well-defined bacteria, such as *E. coli* or a yeast strain. Such hosts are readily transformed and capable of rapid growth and culture. Other unicellular microorganisms, such as fungi or algae, also can be employed. In addition, other forms of bacteria, such as salmonella or pneumococcus, may be substituted for *E. coli*. Whatever host is chosen, it should not contain a restriction enzyme that would cleave the recombinant vector.

If *E. coli* is chosen as a host, a large number of suitable strains are commercially available, including MM294, RR1, HB101, DH1 and JM107. Protocols for a transformation of these hosts are well known, for instance, see Maniatis et al., supra at page 255, and Hanahan (1983) *J. Mol. Biol.* 166:557.

For transformation in yeast, preferably host strains include DB746, DBK747 and 127, which are all common strains of *Saccharomyces cerevisiae* (*S. cerevisiae*). These strains are all widely available, for instance, from the American Type Culture Collection (ATCC), 12301 Parklawn Drive, Rockville, Md. 20852. Procedures for transforming yeast cells with recombinant vectors are well known. For example, see Beggs (1978) *Nature* 275:104-109; Hinnen et al. (1978) *Proc. Natl. Acad. Sci.* (*U.S.A.*) 75:1929-1933; and, Sherman et al. (1979) *Methods in Yeast Genetics*, Cold Spring Harbor Laboratory, Cold Spring Harbor, N.Y.

During transformation, due to limited vector uptake by the cells, only a small portion of the host cells are actually transformed. The cells that have been transformed can be identified by placing the cell culture in agar plates containing suitable growth medium and a phenotypic identifier, discussed above, such as an antibiotic. Only those cells that have the proper resistant gene (e.g., to the antibiotic) will survive. Cells from the colonies that survive can be lysed and then the replicated vector isolated from the lysate. The isolated vectors can be characterized to determine, for instance, the orientation of the cDNA, by digestion with restriction endonucleases and subsequent gel electrophoresis or by other standard methods. Oncce transformed cells are identified, they can be multiplied by established techniques, such as by fermentation.

Assays of Plasmid Recovery

The above-described cloning procedures have been carried out in conjunction with the present invention with plasmid vectors used to transform bacteria (*E. coli*) host and yeast hosts. For example, the present invention has been conducted with the pBR322 plasmid used to transforme *E. coli* RR1 host cells. Also, JM107 *E. coli* host cells have been transformed with recombinant pUC18 plasmids having DNA fragments from the X chromosome inserted therein. Further the present invention has been performed in strain 127 of *S. cerevisiae* transformed with both the YIP5 and YRp7' plasmids.

Plasmid recovery using the foregoing vector/host systems are quantified by three separate assay methods. In a first method, the plasmid-harboring host cells are grown in ampicillin-containing L broth to an optical density, at a wavelength of 600 angstroms ($OD_{600}$), of 0.6 followed by chloramphenicol amplification. Thereafter, the plasmids are purified by the method of Mukhopadhyay and Mandal (1983) *Analyt. Biochem.* 133:265–270. The resulting plasmid preparations typically contain about 40% RNA which is removed by whether of not chloramphenicol amplification was employed. Column D specifies the assay/purification method that was used, with the designation "I-H" indicating the scaled up Ish-Horowitz supra, method and the designation "M&M" indicating the large scale method of Mukhopadhyay and Mandal, supra. The total yield of plasmid containing the X chromosome insert in 500 ml of culture is set forth in Column E. As revealed in Table 1, plasmid numbers 1, 4 and 5 containing the Xrep fragment exhibited a plasmid yield of from 10 to 20 times greater than control plasmids containing similar sized fragments of the X chromosome.

TABLE 1

| | | Recovery of Plasmids in *E. coli* Hosts | | |
|---|---|---|---|---|
| A Plasmid | B Size (Kb) | C Chloramphenicol Amplification | D Method of Purification | E Total Yield Per 500 ml Culture |
| 1. BamR-1 (pBXrep) | 6.7 | Yes | M&M | 9.0 mg |
| 2. BamR-3 | 6.7 | Yes | M&M | 0.8 mg |
| 3. BamR-4 | 6.7 | Yes | M&M | 0.5 mg |
| 4. pUCXrepl | 5.0 | No | I-H | 2.4 mg |
| 5. pUCXrep3 | 5.0 | No | I-H | 1.9 mg |
| 6. pUC10LB | 5.0 | No | I-H | .02 mg |
| 7. pUC4-6LB | 3.0 | No | I-H | 0.25 mg | either RNase treatment or cesium chloride (CsCl) gradient purification. The plasmid yield is determined by ultraviolet absorption spectroscopy. Ultraviolet light absorption is measured at a wavelength of 260 nanometers (nm).

As a spectrophotometric second method, plasmid recovery is also determined by growing the host cells to saturation (i.e. stationary phase) followed by a purification according to the method originated by Ish-Horowicz and Burke (1981) *Nucleic Acids Res.* 9:2989–2998. Thereafter, the RNA is removed from the plasmid DNA by CsCl gradients. After dialysis against ethylene dinitrilotetra-acetic acid ("EDTA"), the plasmid yield is optically read by ultraviolet absorption spectroscopy at 260 nm.

A third less quantitative but simpler method of ascertaining plasmid replication with the present invention employs small scale (approximately 2 milliliter "ml") cultures "mini-preps" of the plasmid-containing host cells. The mini-preps are prepared by the method of Ish-Horowitz and Burke, supra, wherein small volumes (approximately 5 microliters ("ul")) aliquots of each mini-prep are digested with an appropriate restriction enzyme to isolate the cloned DNA. The DNA fragments are then fractionated by agarose gel electrophoresis and photographed under ultraviolet light transillumination.

Results of Cloning with Prokaryotic Hosts

Using the above assays, applicant has found that one of the clones of the genomic DNA, designated as "Xrep" was obtained at a yield from 10 to 20 times greater than other plasmids containing similar size fragments of the X chromosome. As indicated in Table 1 below, the high yield of the Xrep genomic inserts occurred using both the pBR322 and the pUC18 plasmids inserted into *E. coli* hosts. In table 1, the first three plasmids identified in Column A employ the pBR322 vector, whereas the fourth through the seventh plasmids employ the puC18 vector. These vectors were used to transform *E. coli* hosts RR1 and JM107, respectively. The sizes of the recombinant cloning vectors in kb are set forth in Column B. Column C indicates Chloramphenicol amplification of cultures conducted by standard procedures was found to increase the yield of plasmids with and without the Xrep insert indicating that the increase in yield was a phenomenon independent of chloramphenicol stimulation. Applicant also observed that the presence of the Xrep genomic insert did not affect bacterial colony size and that liquid cultures of the host cells grew to the same cell density whether or not the Xrep insert was present in the plasmid. As such, it appears that the increase plasmid yield caused by Xrep is likely due to its effect on plasmid replication activity, stability or maintenance. Further, because the pUC18 and pBR322 plasmids have quite dissimilar sequences flanking the Xrep insert, the enchanced plasmid yield is likely caused by the Xrep fragment itself rather than the result of an accidental combination of the Xrep fragment and the plasmid sequences.

Cloning with Eukaryotic Hosts

The genomic DNA from the X chromosome is also cloned in eukaryotic host vectors, including the yeast vector YIP5, which is commonly used as a test vector for ARS in yeast. See FIG. 3. The details of the cloning procedure are set forth in Example 3 below. The recombinant plasmid is tested for ARS activity in *S. cerevisiae* 127 cells under URA+ selection. When cloning the Xrep fragment with the yeat vector YIP5, the resulting plasmid, designated as pXrYIP2, was found to produce small (1-2 mm), slowly growing colonies suggesting a very weak replicative activity, whereas control hosts transfected with YIP5 plasmid without the Xrep insert resulted in no transformants on -uracil plates after 4 days of culture.

To determine whether X chromosome fragments, including the Xrep insert, would stabilize a plasmid already having an ARS activity, the Xrep fragment was ligated into the YRp7' plasmid. The recombinant emmploying the Xrep insert was designated as pXrYrp, FIG. 4. As set forth in Table 2 below, on the average, 0.36% of the host cells transfected with YRp7' contained plasmid, whereas in separate transfections 4.2% of the host cells contained the recombinant pXrYrp plasmid, which, on the average, is an 11-fold increase. The foregoing indicates that the Xrep insert does not have full ARS activity by itself in yeast hosts, but it does increase significantly the replication or stability of a plasmid in yeast that already contains an ARS element.

In Table 2, plasmids 1 through 5 in Column A contain Xrep, whereas plasmids 6 through 9 do not. Colonies of host cells transformed with plasmids containing Xrep (plasmids 1 through 5) and independent colonies transformed with YRP7' plasmid by itself (plasmid numbers 6–9) were grown on plates lacking tryptophan, suspended and then plated on selective (-Trp) and nonselective (D) medium. The cells lacking plasmid were maintained by cross-feeding and residual gene product. In Table 2, the number of colonies counted are set forth in Column B, whereas the colony forming units per ml are set forth in Column C. As shown in Column D, the percentage of host cells that contain the pXrYrp plasmid was approximately 11 times as great on average as the percentage of host cells that contained the Yrp7' plasmid by itself.

TABLE 2

| A Plasmid | B No. of Colonies Counted | | C Colony Forming Units Per ml ($10^{-4}$) | | D % of Cells With Plasmid |
|---|---|---|---|---|---|
| | D | -Trp | D | -Tpr | |
| 1. pXrYrp-1 | 137 | 45 | 1,370 | 21 | 1.5% |
| 2. pXrYrp-2 | 334 | 174 | 1,670 | 179 | 7.7% |
| 3. pXrYrp-3 | 335 | 271 | 3,350 | 100 | 3.0% |
| 4. pXrYrp-4 | 558 | 379 | 5,580 | 379 | 6.8% |
| 5. pXrXrp-7 | 378 | 27 | 378 | 7 | 2.0% |
| 6. YRp7'-1 | 153 | 23 | 1,530 | 4 | 0.26% |
| 7. YRp7'-2 | 111 | 10 | 1,110 | 5 | 0.45% |
| 8. XRp7'-3 | 307 | 44 | 3,070 | 16 | 0.52% |
| 9. YRp7'-4 | 220 | 19 | 2,200 | 5 | 0.23% |

Characterization of Xrep

The cloned Xrep DNA segment is sequenced using the standard chain termination method originated by Sanger et al. (1977) *Proc. Natl. Acad. Sci. (U.S.A.)* 74:5463–5467, as modified by Smith (1980) *Methods in Enzymology* 65:560–580. Methods for chain termination sequence determination are set forth in the Amersham Handbook entitled, *M13 Cloning and Sequencing*, Blenheim Cresent, London (1983) (hereinafter "Amersham Handbook"); Messing, 2 *Recombinant DNA Technical Bulletin*, NIH Publication No. 79-99, 2, 43–48 (1979); Norrander et al. (1983), *Gene* 26:101; Cerretti et al. (1983), *Nucl. Acids Res.* 11:2599; Biggin et al. (1983) *Proc. Natl. Acad. Sci. (U.S.A.)* 80:3963; and, Smith, supra. In the chain termination method, M13 filamentous phage are employed as a vector to clone the DNA sequence of interest. These phage vectors produce single-stranded DNA templates which are then sequenced by the chain termination method. This sequencing procedure involves priming a single-stranded template molecule with a short primer strand having a free 3' hydroxyl group and then usinng AMV reverse transcriptase to copy the template strand in a chain extension reaction using all four deoxyribonucleotide triphosphates, i.e., dATP, dCTP, dGTP, and dTTP (collectively referred to as "dNTPs"), with one of the dNTPs being radiolabeled. In the synthesis reaction, a nucleotide specific chain terminator lacking a 3'-hydroxyl terminus, for instance, a 2', 3' dideoxynucleotide triphosphate ("ddNTP"), is used to produce a series of different length chain extensions. The terminator has a normal 5' terminus so that it can be incorporated into a growing DNA chain, but lacks a 3' hydroxyl terminus. Once the terminator has been integrated into a DNA chain, no further deoxynucleotide triphosphates can be added so that growth of the chain stops. Four separate synthesizing reactions are carried out each having a ddNTP of one of the four nucleotide dNTPs, i.e., dATP, dCTP, dGTP and dTTP, see Smith, supra. One of the normal dNTPs (dATP) is radiolabeled ($^{35}$S) so that the synthesized strands, after having been sorted by size on a polyacrylamide gel, can be autoradiographed. The chain extensions from the four reactions are placed side by side in separate gel lanes so that the pattern of the fragments from the autoradiography corresponds to the nucleic acid sequence of the cloned DNA. FIGS. 5A, 5B and 5C (collectively "FIG. 5") illustrate the Xrep sequence which is composed of 2,356 bp. In these Figures, the nucleotide bases are numbered beginning with base No. 1. The locations of the various restriction enzyme cleavage sites are indicated.

Figure 6A:
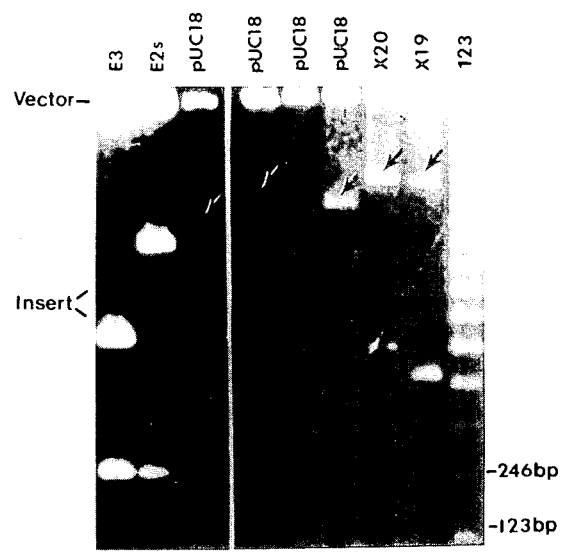
FIGS. 6A and 6B collectively illustrate an ethidium bromide stained agarose-electrophoresis gel slab containing deletion mutants of the Xrep fragment.
Figure 6B:
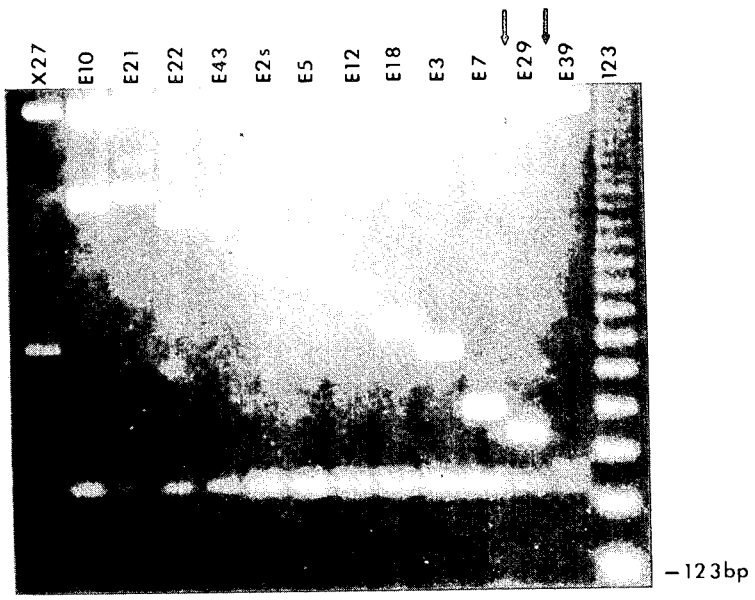

Deletion mutations of the Xrep sequence are prepared to investigate the active sites of the Xrep sequence. The deletion mutants are constructed according to the method of Yoshitake et al. (1985) *Biochemistry* 24:3736–3750. In this method, deletion mutants are constructed by double digestion of the pUC18 polylinker region, for instance with Pst I and Xba I restriction endonucleases, so that exonuclease III can be used to systematically degrade the Xrep insert without affecting the plasmid sequences. The exonuclease III digestion is followed by S1 nuclease treatment and then ligation of the resulting blunt-ended molecules. Subsequent transformation of the host, JM107, results in the direct cloning of the various deletion mutants. The various deletion fragments are analyzed by gel electrophoresis and ethidium bromide staining and photography as shown in FIGS. 6A and 6B. Also, the deletion mutants are analyzed by standard restriction enzyme mapping and by dideoxy sequencying as discussed above. The results of this analysis are set forth in FIG. 7.

In the ethidium bromide stained gel shown in FIGS. 6A and 6B, the top band (of 2.4 kb) was derived entirely from the vector which had been digested with Pvu II. Since different sized DNA fragments proportionally bind different amounts of ethidium bromide, the identical 2.4 kb top bands in each aliquot were used for comparative purposes. The variable sized, middle bands of the aliquots represent various deletion mutant inserts. Residual, uncut supercoiled molecules are indicated by the arrows in FIG. 6A.

The DNA fragments shown in the photographs of FIGS. 6A and 6B, along with other deletion mutation fragments, are schematically shown in FIG. 7. In FIG. 7, Section A consists of a restriction enzyme cleavage map of Xrep. The large open box indicates the cluster of enhancer-like sequences (ELS) found in the region of the Xrep fragment. The various restriction enzyme cleavage sites are indicated.

In Section B of FIG. 7, the numbers between the tick-marks indicate the percent of the combined guanine (G) bases and cytosine (C) bases for each 120 bp segment extending along the Xrep segment.

Section D of FIG. 7 illustrates the composition of the various deletion mutants of the Xrep which were constructed. From the plasmid recovery assays two regions of the Xrep, designated as alpha and beta in Section C, FIG. 7, were found to be important in the activity of the Xrep. The alpha and beta regions are labeled in FIG. 5, i.e., nucleic acid Nos. 1 through 940 and nucleic acid Nos. 1961 to 2170, respectively. As shown by the upper bands of FIGS. 6A and 6B, the plasmids which lacked the alpha region but contained the beta region (the "En" series of plasmids, of FIG. 6B) retained a residual positive effect. However, this effect decreased when sequences near the left end of subclone E29 were deleted. As such, subclone E29 defines the left or upstream border of the beta region.

A further finding, as illustrated by subclones X19, X20 and X27, was that the alpha region had little or no positive effect by itself, i.e., in the absence of the beta region. Although not shown in the stained agarose gel of FIGS. 6A and 6B, the subclones Os4 and Os50 contained the entire alpha region shown in FIG. 7; these subclones did not produce elevated levels of plasmid. The assays did, however, establish that the alpha region increases the effectiveness of the beta region of the Xrep by about 2-3 fold.

The nucleotide sequence of the Xrep set forth in FIG. 5 was compared by computer analysis with other known nucleotide sequences. The search revealed that an approximate 750 bp region of Xrep contains numerous close homologies with known enhancer sequences. This region of the Xrep has been labeled as ELS in FIGS. 5 and 7. One of the homologies that was discovered was that the ELS region contained four copies of the so-called Ela enhancer core sequence:

CTTCCT
GAAGGA which is found in viral DNA. See for example, Herbomel et al. (1984) Cell 39: 653-662. These four Ela enhancer core sequences are labeled as Nos. 2, 3, 4 and 5 in FIG. 5, with the number 2 sequence being on the complementary strand. Statistically, it is likely that one of these hexameric core sequences would occur about once every 4,100 bp. Maniatis et al., supra at p. 4. Thus, the existence of four such sequences within the ELS region may be significant.

The ELS region also contains the sequence:

CTATTTGCCACA
GATAAACGGTGT

This sequence is distinct from the Ela enhancer core sequence but resembles the enhancer core sequence of $SV_{40}$. Herbomel et al., supra. This 12-mer sequence has been labeled as No. 1 in FIG. 5. In addition to the foregoing, the ELS region was found to have two 11-mers at nucleotides 165-175 and 462-472 in FIG. 5 which are identical with repeats found in the SV40 and BK virus enhancers, respectively. See Gruss et al. (1981) Proc. Natl. Acad. Sci. (U.S.A.) 78:943; and, Rosenthal et al., supra, respectively.

Also within the ELS region, a 19 bp true palindrome was found having a sequence quite similar to true palindromes located near the replication origins of the SV40, BK and polyoma viruses. Soeda et al. (1979) Cell 17:357-370. The true palindrome is labeled in FIG. 5. A comparison of the Xrep palindrome with those of the SV40, BK and polyoma viruses is set forth in FIG. 8A. Using equations originated by Day and Blake (1982) Nucl. Acids Res. 10:8323-8339, applicant estimates that the probability of finding a 19 bp true palindrome any- where in the Xrep sequence is about 0.01 and within the ELS region the probability is about 0.002.

A significant finding was the juxtaposition of the true palindrome, a 17 bp sequence similar to a 17 bp sequence found in BK virus, and the enhancer-like sequences (FIG. 8B). This similarity of sequence arrangements comparing Xrep and DNA viruses undoubtedly plays a role in the function of Xrep in human cells and therefore may play an important role in applications of Xrep in mallalian cell plasmids. However, the most important part of the Xrep sequence, as regards effects seen on prokaryotic plasmid yield, was determined to be the Xrep beta sequence (above), which bears no similarity to known sequences in extensive computer assisted searches.

Despite the similarities of the ELS region and the foregoing viral replication origins, there is at least one substantial difference therebetween. The A/T rich region found within the replication origins of the BK, polyoma, and SV40 viruses, is not found near 19 bp true palindrome of Xrep. These A/T rich regions appear to be an important part of the replication origins of, at least, the SV40 virus in that deletion of this region adversely affects SV40 viral replication.

Expression of Functional Protein Product

Applicant has discovered that the Xrep fragment is capable of inducing increased expression of functional protein products. An exemplary expression system of the present invention involves the use of the Xrep fragment to produce increased expression of the CAT enzyme in mammalian cells. The CAT activity is easily and completely distinguishable from any endogenous activities and when used in conjunction with monkey COS-1 cells, there is no interference from other enzymatic activities which could compete for the substrate used in the CAT assay.

Figures 9A, 9B:
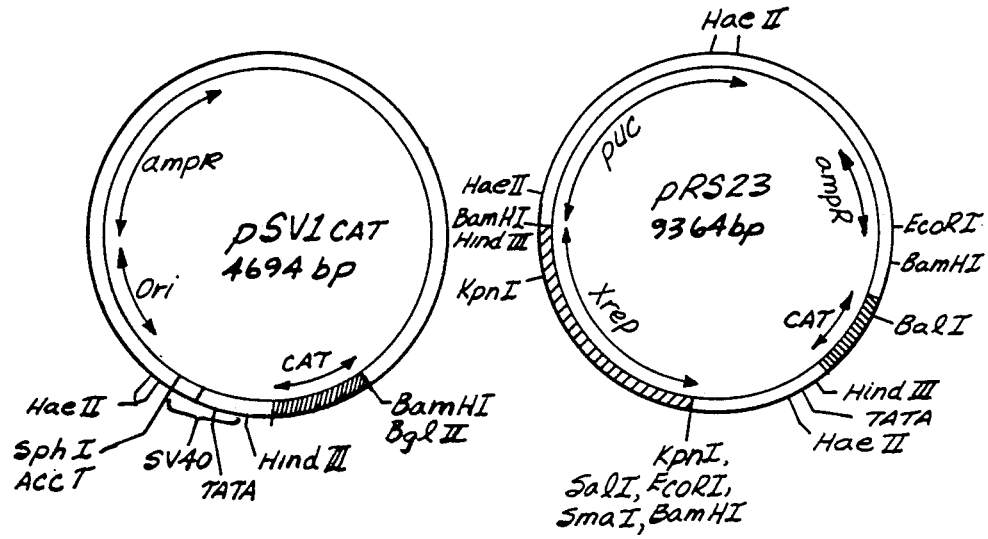

In the expression procedure, the Xrep was inserted between the two Hae II sites of plasmid pSV1.CAT to form plasmid pRS23, see FIGS. 9A and 9B. The construction of the pSV1.CAT plasmid is set forth in Gorman et al. (1982) Mol. Cell. Biol. 2:1044-1051, incorporated herein by reference, and is illustrated in FIG. 9A. As shown in FIG. 9A, the pSV1.CAT plasmid contains the origin of replication and the ampicillin resistant gene from plasmid pBR322. The plasmid also includes 30% of one of the 72 bp promoter repeats from the wild-type SV40 and a Goldberg-Hogness TATA box. Of course, the plasmid contains the prokaryotic CAT gene which is shown in solid line in FIG. 9. To form the pRS23 plasmid, the plasmid pUCXrep1 (FIG. 2) was partially digested with Hae II. The resulting linear 5 kb fragment was inserted into the Hae II site of pSV1.CAT yielding the recombinant pRS23. As shown in FIG. 9B, when the Xrep is inserted into the Hae II site in the pSV1.CAT plasmid, it is positioned 5' to the CAT gene.

The Xrep fragment was also inserted into the BamH I site of the pSV1.CAT plasmid. This site is located 1.5 kb 3' to the CAT gene, FIG. 9C. The resulting plasmid has been designated as pSCR5. The 2.3 kb BamH I Xrep fragment (whole Xrep) was released from pUCXrep1 using BamH I prior to ligation with BamH I cut pSV1.CAT.

Also, plasmid pRS23 was treated with the enzyme KpnI which released the 1.6 KpnI Xrep fragment. Ligation then produced the plasmid, pRE9, which was subcloned (i.e., isolated and amplified). As shown in FIG.

9D, this plasmid contains the enhancer homologous region of Xrep located at a position 5' to the CAT gene.

As shown in FIGS. 9A–9D, the pSV1.CAT vector and the recombinant vectors prepared therefrom containing the Xrep each include the $Amp^R$ cistron, the origin of replication from pBR322 and approximately 30% of one of the 72 bp repeats of the SV40 early promoter region, together with the Goldberg-Hogness TATA box.

The foregoing recombinant vectors were transformed into monkey COS-1 cells in logarithmic phase growth. Following an incubation period after transfection, the host COS-1 cells were harvested, extracts made therefrom and then assayed for CAT activity by thin layer chromatography according to the method detailed in Gorman et al., supra. As a control, the pSV1.CAT plasmid by itself was also used to transfect the COS-1 cells. As a further control, a second plasmid designated as pSV2.CAT was also employed to transfect COS-1 cells. As illustrated in FIG. 9E the pSV2.CAT plasmid is similar to the pSV1.CAT plasmid with the exception that the pSV2.CAT plasmid has both of the 72 bp enhancer sequences of the early promoter region SV40 viral DNA.

The control plasmid, pSV1.CAT, was found to result in about a three-fold transcriptional enhancement relative to background (COS-1 cell extracts after mock transfections with no DNA). Both the pRS23 plasmid (Xrep 5' to the CAT gene) and the pRE9 plasmid (ELS 5' to the CAT gene) yielded a four to six-fold increase of CAT activity over the activity level produced by the control pSV1.CAT plasmid (the plasmid with a partial SV40 enhancer). The pSV2.CAT plasmid resulted in an increase of CAT activity similar to that provided by the pRS23 and the pRE9 plasmids. Thus, the Xrep/ELS region appears to have the same potency as a complete set of the two 72 bp enhancers of SV40. The plasmid pSCR5 (Xrep 3' to CAT gene) resulted in an increase of CAT activity of about two to three-fold over the activity level of the control pSV1.CAT plasmid.

The increase in CAT activity provided by the Xrep confirms the ability of the Xrep to increase expression of protein products even above the expression levels obtainable with high level promoters such as that contained in the SV40 origin of replication region, since all of the foregoing constructs, including the pSV1.CAT plasmid contained this origin of replication region. The observation that the Xrep inserted 5' to the CAT gene resulted in two to three times the stimulation of the 3' construct, pSCR5, suggest an effect on transcription. The strong enhancer-like effect of the ELS region (pRE9) in the absence of the beta region supports this interpretation.

The process and products of the present invention are further illustrated by the foregoing examples.

EXAMPLE A

Spectrophotometric Assay No. 1

This assay ascertains the quantity of DNA present by measuring the amount of ultraviolet light at wavelength 260 nm absorbed by the DNA. This assay was employed to monitor the ability of the Xrep to enhance a vector replication.

In the assay, host cells were grown in L broth and ampicillin (50 ug/ml) at 37° C. with gentle shaking until the optical density of the culture at 600 nm reached 0.6. Next, L broth at two times volume and ampicillin at 50 ug/ml were added to the late log culture. Thereafter, the culture was incubated at 37° C. for 2.5 hours with vigorous shaking.

The culture was then amplified by addition of 2.5 ml of 34 mg/ml chloramphenicol (in ethanol) to each 500 ml of culture. The cells were then incubated overnight at 37° C. with gentle shaking. Next, the plasmid DNA was isolated from the E. coli host cells. To this end, the cell cultures were harvested in two separate 250 ml clear plastic centrifuge (cf) bottles, and then the cultures were centrifuged at 5,000 rpm (GS-34 rotor) at 4° C. for ten minutes. Thereafter, the supernatants were discarded and 2 pellets from each culture were resuspended in a total volume of 150 ml of buffer A (50 mM Tris-HCl, 5 ml EDTA, 5 ml NaCl, pH 8) on ice at 4° C. This mixture was then recentrifuged and the resulting supernatant discarded and the pellet resuspended at 4° C. in 7.5 ml Buffer A, together with 25% sucrose on ice.

Thereafter, in the absence of direct light and on ice, the suspended cultures were placed in a type 60 Ti centrifuge tube having a volume of approximately 25 ml, together with 1.5 ml of 5 mg/ml lysozyme and 5 mg/ml of ethidium bromide (EtBr). The mixture was then placed on ice for five minutes. Thereafter, 3 ml of 0.25 $Na_2EDTA$ (pH 8), was added and mixed gently, and the resulting mixture placed on ice for five minutes. Next, 12 ml of lysis mixture (1% Brij 58, Sigma Chemical Company, St. Louis, Mo.), 0.4% sodium deoxycholate, 62 mM $Na_2EDTA$, 50 mM Tris-HCl (pH 8) was added and mixed thoroughly, but gently, with the resulting mixture incubated on ice for 30 minutes with occasional, gentle stirring. The slightly viscous, total lysate was then centrifuged at 48,000×g for 25 minutes. The resulting, clear, reddish supernatant was removed with a pipette and placed in a 150 ml Corex bottle, warmed briefly to 37° C. Then, a 1/9 volume of 100 mM EDTA containing 1% SDS and 1/18 volume of 10 mg/ml proteinase K were added and thereafter the mixture incubated at 37° C. for one hour. This procedure assists in deproteinizing the plasmid DNA.

Next, the resulting lysate was further deproteinized by double phenol extraction. One-half volume of pH 5.0 buffer equilibrated phenol and one half volume of chloroform was added. After emulsification, the extract was centrifuged at 1500×g for five minutes and the organic phase removed. This process was repeated two times followed by two extractions with one volume of chloroform alone. Salt (NaCl) was added to 0.3M followed by two volumes of ethanol to precipitate the DNA. The DNA was pelleted, dried and suspended in 0.3 ml of 0.2 mM EDTA. Thereafter, the RNA was removed from the deproteinized material by RNase treatment.

Next, the resulting pellet was suspended in 0.3 ml of EDTA and solubilized for one hour at 37° C. One ul of the resulting purified chromosomal DNA was placed in 1 ml of distilled water. Thereafter, the ultraviolet light absorbance at 260 nm and at 280 nm wavelengths were measured to ascertain the quantity and purity of the DNA material, with pure E. coli DNA having a $A_{260}/A_{280}$ ratio of 1.95.

EXAMPLE B

Spectrophotometric Assay No. 2

In this assay, the host cells were grown to saturation and then purified by the Ish-Horowitz and Burke method, supra, followed by equilibrium sedimentation in CsCl gradients. Thereafter, the plasmid yield was measured by ultraviolet absorption spectroscopy in the same manner detailed above in Example A.

Briefly, the host cells were grown to saturation using the same procedures discussed above in Example A. Thereupon, 100 ml of the saturated culture was harvested by centrifugation at 1500×g at 4° C. for 10 minutes. The culture concentrate was resuspended in 10 ml of 50 mM glucose, 25 mM Tris (pH 8), 10 mM EDTA containing 5 mg/ml lysozyme, and then incubated for five minutes at 22° C. Next, 20 ml of 0.2N NaOH, and 1% sodium dodecyl sulfate (SDS) were added by gentle mixing and then the resulting mixture placed on ice for five minutes. 15 ml of precooled 5M KOAc (pH4.8) was added by gentle mixing, and then after five minutes on ice, the precipitated protein, SDS and chromosomal DNA were removed by centrifugation for five minutes. To the supernatant 250 ul of diethylpyrocarbonate (DEPC) was added, the mixture shaken and then heated at 65° C. for 20 minutes. Following centrifugation, two volumes of EtOH was added to the supernatant, chilled for one hour on ice and then the plasmid DNA precipated with a five minute centrifugation. The resulting pellet was then washed with 70% EtOH, dried, and then taken up in 50 ul of TE (10 mM Tris Cl [pH 8.0] and 1 mM EDTA [pH 8.0]).

Thereafter, the RNA was removed by CsCl gradient purification in the same manner discussed above in Example A. After dialysis against 0.2 mM EDTA (pH 7.0), the yield of resulting plasmid was determined by measuring ultraviolet light absorbance at 260 nm and 280 nm as discussed above in Example A, to measure both the quantity and purity of the plasmid.

EXAMPLE C

Mini-Prep

A third assay method, though less quantitative than the two methods detailed above, was simple enough to permit quantitation of the various Xrep constructs.

Briefly, this method used the same Ish-Horowitz and Burke purification procedure employed in Example B, but in small-scale, 2 ml cultures of plasmid-containing host cells. 5 ul aliquots of each mini-prep were digested with appropriate restriction enzymes by standard methods, for instance as set forth in Maniatis et al., supra, beginning at page 98. The digests were analyzed on 0.75% agarose gels stained with 0.25 ul/ml EtBr followed by photography under ultraviolet transillumination.

EXAMPLE D

Nucleotide Sequencing

The various DNA fragments employed in the present invention, including the Xrep and mutants thereof, were sequenced by the standard chain termination method, essentially as described in the Amersham Handbook, supra, with the variations set forth below. The DNA of interest, digested with Hind III and EcoR1 restriction enzymes, were subcloned into strains mp18 and mp19 of the M13 single-stranded filamentous phage vector (Amersham, Arlington Heights, Ill.). The mp18 and mp·phage vectors, as set forth in Norrander et al., supra, contain the following unique cloning sites: Hind III; Sph I; Pst I; Sal I; Acc I; Hinc II; Xba I; BamH I; Xma I; Sma I; Kpn I; Sst I; and, EcoRI. The composition of the mp18 and mp19 vectors are identical, with the exception that the order of the above-identified restriction sites are reversed in the mp19 vector so that both strands of the cDNA insert may be conveniently sequenced with the two vectors to resolve any sequence ambiguities. The mp18 and mp19 vectors, with a corresponding strand of the cDNA inserted therein, were used to transform E. coli JM107 of the strain K12 (Bethesda Research Laboratories, Bethesda, Md.) to produce replicate single-stranded DNA templates containing single-stranded inserts of the sense and antisense strands.

The synthetic universal primer: 5'-GTAAAAC-GACGGCCAGT-3' (Amersham Co.) was annealed to the single-strand DNA templates and used to prime DNA synthesis with AMV reverse transcriptase at 55° C. using dideoxnucleotides and deoxynucleotides. Thereafter, the extension fragments were size-separated by gel electrophoresis and autoradiographed from which the nucleotide sequences of the fragments were deduced.

Deoxyadenosine 5' (alpha-[$^{35}$S] thio) triphosphate (hereinafter "dATP [alpha-$^{35}$S]") was used as the radioactive label in the dideoxy sequencing reactions. Also, rather than using the gel set forth at page 36 of the Amersham Handbook, a 6% polyacrylamide gel was employed (6% polyacrylmide gel, 0.4 mm thick, containing 7M urea, 100 mM Tris borate [pH 8.1], and 2 mM EDTA).

EXAMPLE 1

Cloning of the Xrep Sequence in Bacteria Host E. coli RRI

The human lymphoblast cell line, GM1416, was propagated in Eagle's minimal medium supplemented with 10% (v/v) fetal calf serum (FCS) and 40 ug/ml gentamicin in a humidified atmosphere of 5% $CO_2$ in air. Viable cells were harvested and then total genomic DNA prepared therefrom by standard methods. See, for example, Riley, Canfield and Gartler (1984), *Nucl. Acids Res.* 12:1829–1845.

The genomic DNA was digested with the restriction enzyme BamH I by mixing 50 ug of the genomic DNA with 105 units of BamH I restriction endonuclease (Bethesda Research Laboratories, Bethesda, Md. ("BRL")) and the buffer recommended by the manufacturer. Incubation was at 37° C. for three hours. The DNA fragments were fractionated into size classes by electrophoresis on agarose gel. The DNA fragments migrating in the agarose 0.75% gel in the 1.9–2.3 kb region were excised, electro-eluted from the gel, and then cloned into the BamH I site of the pBR322 plasmid to form plasmid pUCXrep, as illustrated in FIG. 1. In FIG. 1, the sequences from pBR322 are shown in thin line whereas the Xrep fragment is shown in thick darkened line.

In the cloning procedure, 1.0 ug of plasmid pBR322 (BRL) was prepared for ligation by digestion with 10.5 units BamH I restriction endonuclease. The BamH I treated pBR322 was treated with 0.025 units calf intestinal alkaline phosphatase (BRL) for 2.5 hr. at 37° C. followed by phenol extraction and ethanol precipitation as described previously. One ug of the so treated pBR322 was mixed with 1 ug of the electroeluted BamH I treated genomic DNA and the mixture ligated with T4 DNA ligase (1 unit, BRL) 37° C. for two hours.

The above reaction employed T4 DNA ligase buffer as recommended by the manufacturer. Ten×T4 DNA ligase buffer (tenfold concentration) is composed of 25 mM Tris (pH 7.4), 10 mM $MgCl_2$, 1 mM dithiothreitol, and 0.4 mM andeosine triphosphate (ATP). The mixture was incubated overnight at 15° C.

The resulting recombinant plasmids, originally designated as the BamR-1 series and later renamed as pBXrep, was then transformed into *E. coli* strain RR1, using standard transformation techniques, such as disclosed by Maniatis et al., supra.

The host cells were grown on agar plates selective for ampicillin resistance and then the transformed cells were identified and amplified by standard techniques, including chloramphenicol stimulation. The quantity of plasmid present in cultures derived from host cell colonies was analyzed by the assay procedures discussed above. The Xrep containing plasmid clone was produced by host cells at 10 to 20 times the amount of the other BamR-n series plasmids. The overproduced plasmid pBXrep became the focus of further study and development. The Xrep segment was removed from the plasmid by digestion by BamH I restriction endonuclease and then analyzed by restriction enzyme mapping and nucleic acid sequencing, as discussed above.

EXAMPLE 2

Cloning of the Xrep Sequence In Bacteria Host *E. coli* JM107

The Xrep sequence described above was also cloned in plasmid pUC18, see FIG. 2 and then the recombinant vector used to transform *E. coli* JM107 host cells. In FIG. 2, the sequences from pUC18 are shown in thin line whereas the Xrep is shown in thick darkened line. In the cloning procedure, 20 ug of plasmid pUC18 (obtained from J. Messing, Rutger's University—also available from BRL) was prepared for ligation by digestion with 40 units BamH I restriction endonuclease (BRL) using the buffer and reaction conditions (37° C.) specified by the manufacturer. Following four hours of BamH I digestion, the BamH I cut pUC18 DNA was treated with 10 mM EDTA (final), 0.1% SDS and 0.2 mg/ml proteinase K (Boehringer Manheim Biochemicals, Indianapolis, Ind.) for one hour at 37° C. The sample was then phenol-chloroform extracted and ethanol precipitated as described above.

The plasmid pBXrep described above was also treated with BamH I and processed identically to the BamH I cut pUC18 described above. The BamH I cut pBXrep and pUC18 DNAs were mixed and ligated randomly under conditions described above for the construction of pBXrep.

The latter ligation generated every possible combination of the three BamH I DNA fragments (two from pBXrep-vectors inserts; and one from pUC18). Competent JM107 bacterial cells were mixed with the ligated mixture incubated on ice for 30 minutes, heat-shocked at 42° C. for two minutes, outgrown in rich medium (2XYT) for one hour and plated on 2XYT agar plates containing ampicillin, X-gal and isopropyl-$\beta$-D-thiogalactopyronoside (IPTG) (See Yanish-Perron, Vieira and Messing, 1985 *Gene* 33:103 and references cited therein for details on JM107, 2XYT, X-gal and IPTG. 16 hours later, white colonies were picked (blue colonies contain empty pUC18 plasmids i.e., clones carrying no foreign DNA). White colonies contain other recombinants with the ampicillin resistance gene of pUC18 or pBR322. The white colonies were miniprepped and the DNA cut with BamH I and run on agarose gels. Two colonies (clones) had fragments corresponding in size to pUC18-Xrep recombinants (FIG. 2). The quantity of plasmid present in the host cells was analyzed by assay procedures discussed above. Also, the Xrep segment was removed from the plasmid by digestion with BamH I restriction endonuclease and then analyzed by restriction enzyme mapping and nucleic acid sequencing, as set forth above.

EXAMPLE 3

Cloning of Xrep Gene Employing Yeast Integrating Plasmid Vector

As shown in FIG. 3, the Xrep was ligated into the plasmid YIP5 to form the recombinant vector pXrYIP2 for ascertaining replication in *S. cerevisiae* 127 host cells. The YIP5 plasmid is commonly used as a test vector for ARS in yeast.

Xrep DNA and the YIP5 plasmid were prepared for ligation with the Xrep gene as discussed above in Example 1. The YIP5 plasmid is accessible through Botstein and Davis (1982), *The Molecular Biology of the Yeast Saccharomyces*. Eds. Strathern et al., Cold Spring Harbor Laboratory, Cold Spring Harbor, N.Y. and references cited therein. As shown in FIG. 3, the resulting pXrYIP2 plasmid includes an origin of replication, and ampicillin resistant gene ($Ap_r$) and a tetracycline resistant gene ($Tc_r$) from plasmid pBR322 to permit maintenance of the plasmid and selection of desired recombinant plasmids in *E. coli*. The plasmid also contains the URA 3 gene to serve as a selectable marker in yeast. In addition, this plasmid has a unique BamH I restriction enzyme cleavage site. The Xrep fragment was ligated to the linearized YIP5 plasmid using the procedures set forth in Example 1 to form the recombinant pXrYIP2 plasmid.

The pXrYIP2 plasmid was transformed into yeast strain 127 (ADEL 2, LEU 2, TRY 1, URA 3, CAN 1, CYH 2, MAT A) of *S. cerevisiae* for selection of URA+ transformants by standard techniques described by Hinnen et al., supra. Prior to transformation, the strain 127 was grown in culture in YEPD medium to mid-log phase ($O.D._{661}=3.0$ [1:10 dilution=0.3]). YEPD medium is composed of 1% (wt/vol) yeast extract, 2% (wt/vol) peptone, 2% (wt/vol) glucose. The cells were harvested by centrifugation at 5,000×g for five minutes at 22° C., and then the resulting pellet was washed with sterile, distilled water, and resuspended in 10–20 ml SE buffer, pH 8.0. SE buffer is composed of 1M sorbitol and 20 mM ETDA, pH 8. The yeast cells were then combined into a single centrifuge tube and spun at 5,000×g for five minutes at 22° C. The resulting pellet was resuspended in 10 ml of SE and then 10 ul of stock ZME (approximately 50 mM final ZME with cells) was added. ZME is composed of zymolase, 10 mg/ml, 10 mM 2-mercaptoethanol and 10 mM EDTA. The resuspended cells were incubated at room temperature for ten minutes and then centrifuged at 5,000×g for five minutes. The cells were washed once with SCE, pH 5.8, and then centrifuged at 5,000×g for five minutes. SCE is composed of 1M sorbitol, 0.1M sodium citrate (pH 8.5), 0.02M ETDA. Thereafter, the cells were resuspended in 10 ml of SCE. Glusulase, to break down the cell walls, in an amount of 0.05% to 0.1% was added to the solution and then the solution incubated at 30° C. for 40 minutes with occasional gentle shaking. The presence of spheroplasts was assayed by diluting 10 ul of the yeast cells with 90 ul of lysis buffer and then viewing 10 ul of this mixture under a light microscope at 400× phase contrast to observe for "ghosts" until 60% of the cells were dark. Lysis buffer is composed of 50 mM Tris, 20 mM ETDA and 3% Sarkosyl, pH 9.0. The cell mixture was then centrifuged at 300×g for ten minutes. The resulting pellet was twice washed with 1/10 volume of SCa and then spun at 300×g for ten minutes. SCa is composed of 1M sorbitol and 10 mM CaCl$_2$.

The yeast spheroplasts from *S. cerevisiae* 127 were then transformed with the previously prepared plasmid vector in accordance with the method of Hinnen et al., supra. The pelleted spheroplasts were suspended in 1/200 volume of SCa and then divided into 100 ul aliquots in 1.5 ml Eppendorf tubes. Then, from 1 to 10 ml of the plasmid DNA were added to each aliquot (0.5 to 5 ug). The mixture was incubated at room temperature for 15 minutes and then 1 ml of PEG (20% PEG 4,000, 10 mM CaCl$_2$, 10 mM Tris-HCl [pH 7.4]) was added to each aliquot to promote DNA uptake. After fifteen minutes at room temperature, the mixture was centrifuged for five minutes at 350×g. The resulting pellet was resuspended in 150 ul of SOS (10 ml of 2M sorbitol, 6.7 ml of YEP [1% (wt/vol) yeast extract, 2% (wt/vol) peptone, 2% (wt/vol) glucose], 0.13 ml of 1M CaCl$_2$, 27 ul of 1% tryptophane and 3.7 ml of H$_2$O). This mixture was incubated for twenty minutes at 30° C. The cells are then plated on agar plates previously poured from the following mixture: 90 g of yeast extract, 180 g of peptone, 180 g of agar, 180 g of dextrose and 9 l of distilled water. The plates were incubated from two to four days at 30° C. Colonies which developed in -uracil medium contained plasmids that have the Ura-3 gene, i.e., those that were transformed.

As a control, the *S. cerevisiae* 127 strain was transfected with the YIP5 plasmid by itself. As noted above, this resulted in no transformants on -uracil plates after four days of incubation at 30° C. On the other hand, the pXrYIP2 plasmids produced small (1–2 mm) slowly growing colonies suggesting weak replicative activity.

EXAMPLE 4

Cloning of Xrep Gene Employing Plasmid Vector Exhibiting ARS Activity

As shown in FIG. 4, the Xrep was ligated into the BamH I site of the ARS yeast plasmid YRp7' using the methods discussed above in Example 1 to form plasmid pXrYrp. The YRp7' plasmid, which is accessible through, for instance, Stinchcomb et al. (1979) *Nature* 282:39–43, includes a ColE1 origin of replication, and an ampicillin resistant gene (Ap$^r$) from plasmid pBR322 to permit maintenance of the plasmid and selection of desired recombinant plasmids in *E. coli*. The plasmid also contains the Trp-4 gene to serve as a selectable marker in yeast as well as the yeast ARS1 sequence which serves as a replication origin in yeast. In addition, this plasmid has a unique BamH I restriction enzyme cleavage site.

The Xrep fragment was ligated into the linearized YRp7' plasmid using the procedures set forth in Example 1 to form the recombinant pXrYrp plasmid. This recombinant plasmid was transformed into *S. cerevisiae* 127 host cells using the procedures detailed in Example 3 with the plating of the transformed cells taking place on selective (-tryptophane) and nonselective media to determine the percentage of host cells containing the pXrYrp plasmid. As a control, *S. cerevisiae* host cells were also transfected with YRp7' plasmid by itself in selective (-tryptophane) and nonselective media. As noted above, on the average, the pXrYrp plasmid was maintained in host cells at a rate on the average of 11 times greater than in host cells transformed with YRp7' plasmid by itself. Thus, although the Xrep does not have the full ARS activity by itself in yeast as evidenced by the Y1P5 experiments, it does significantly increase the replication or stability of a plasmid that already contains an ARS element.

EXAMPLE 5

Construction of Xrep Deletion Mutants

Xrep mutants were prepared by sequential deletion at the 3' end of one strand with exonuclease III using the procedure set forth in Yoshitake et al., supra. Briefly, the deletion mutants were constructed by double digestion of the pUC18 polylinker region of pUCXrep with selected restriction enzymes, e.g., Pst I and Xba I in such a manner that a 3' overhang resistant to exonuclease III was formed in the linearized DNA near the plasmid sequences whereas a recessed 3' end was formed near the Xrep sequences, thereby exposing such end to exonuclease III digestion. A typical sequential digestion of the Xrep fragment with exonuclease III was carried out by incubating 28.3 ug of Xrep DNA with exonuclease III (1.7 units/ug) in 0.17 ml of 1× special exonuclease buffer composed of 10 mM Tris, 1 mM MgCl$_2$ and 1 mM of 2-mercaptoethanol, pH 8.0. Under these conditions, the Xrep fragment was sequentially deleted on one strand at the 3' end at an average rate of about 16 bases per minute. Agarose gel analysis revealed that these conditions led to an evenly spread size distribution corresponding to deletions of Xrep in the range from zero to 2,300 bases. After one hour at 37° C., the mixture was immediately mixed with 1/9 volume of 10×S1 nuclease buffer. 1×S1 nuclease buffer (30 mM potassium acetate, 0.25 NaCl, 1 mM zinc acetate, pH 5.0). After heating to 65° C. for 15 minutes, S1 nuclease was then added to each aliquot (one unit/ug of DNA), and the incubation continued for 45 minutes at 45° C. The reaction was terminated by the addition of Tris (pH 7.4) to 0.1M, EDTA to 10 mM, SDS to 0.1% and proteinase K to 0.2 mg/ml for one hour at 37° C. The samples were then phenol-chloroform extracted, chloroform extracted and ethanol precipitated as described in Example A. End filling-in with Klenow fragment prior to ligation was found not to be necessary.

Subsequent ligation of the S1 treated molecules led to the generation of over one hundred different deletion mutants each still containing the pUC18 ColE1 origin and ampicillin resistance genes. These mutant clones were identified by miniprepping and restriction mapping many of the randomly selected colonies.

Thereafter, the plasmid recovery from the transformed host cells were assayed by the methods set forth above in Examples A, B and C. Also, the nucleic acid sequences of the mutants were analyzed as discussed above in Example D. The results of the assays and the DNA sequence analysis have been discussed above.

EXAMPLE 6

Expression of Protein Product Using Xrep Insert

The Xrep fragment was inserted between the two Hae II restriction enzyme cleavage sites located 5' to the CAT gene of plasmid pSV1.CAT using standard techniques to form the recombinant structure pRS23, see FIG. 9B. As shown in FIG. 9A, the pSV1.CAT plasmid was derived from pBR322, the bacterial CAT gene and SV40. See Gorman et al., 1982, supra and references cited therein, and Gorman et al. (1983) *Sci-* ence 221: 551–553. The plasmid includes the origin of replication and Amp® gene from pBR322 and also part of the control region of the SV40 plasmid, including 30% of one of the 72 bp repeats of the early promoter region (heavy line) and an intact Goldberg-Hogness TATA box. The pSV1.CAT plasmid is commonly employed as a plasmid to investigate the function of various enhancers in eukaryotic systems. Monitoring the enzymatic activity resulting from the expression of the CAT gene provides a convenient method of measuring enhancer activities in mammalian tissue culture cells.

Figures 9C, 9D:
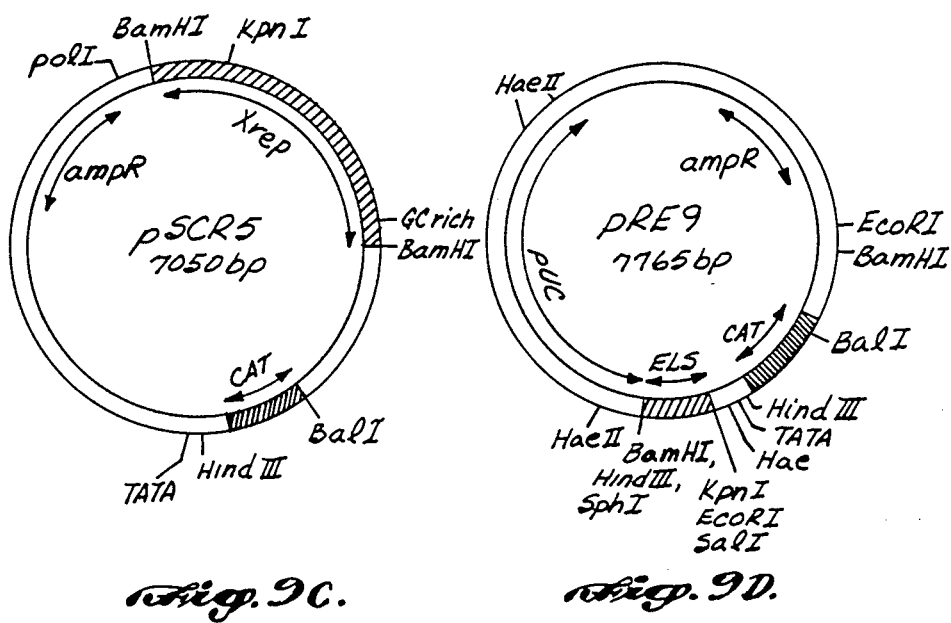
Figure 9E:
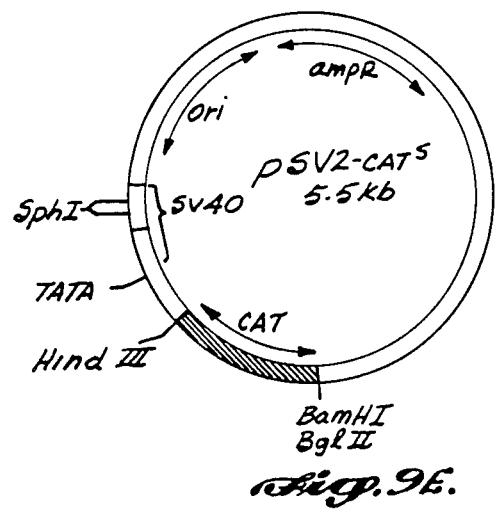

To analyze the enhancer activity of the Xrep fragment, in addition to inserting the Xrep 5' to the CAT gene in plasmid pSV1.CAT, standard procedures were used to insert the Xrep fragment into the BamH I restriction enzyme cleavage site located 3' to the CAT gene to form construct pSCR5, see FIG. 9C. In addition, a 753 bp section of the ESL region (from BamH I to Kpn I) was inserted into the restriction enzyme cleavage site located 5' to the CAT gene to form the construct pRE9, see FIG. 9D.

To form the recombinant vector pRS23, the plasmid pUCXrep1 was opened at the asterisk marked Hae II site (FIG. 2) by partial Hae II digestion and inserted into Hae II cut and phosphated pSV1.CAT plasmid by standard methods.

To form the pSCR5 construct, the Xrep was ligated into the BamH I site located at 3' end of the CAT gene in plasmid pSV1.CAT. The ligation details are essentially identical to those described in Example 1. Recombinants were analyzed by mini-prep and agarose gel analysis of restriction fragments.

To form the pRE9 construct, plasmid pRS23 was digested with the enzyme Kpn I which released the 1.6 kb fragment between the Kpn I site of Xrep and the Kpn I site of the pU18 polylinker (FIG. 9B). Religation resulted in the deletion of all but the 753 bp BamH I to Kpn I fragment of Xrep. Thus, plasmid pRE9 containing the enhancer-like portion of Xrep was formed.

The foregoing Xrep/pSV1.CAT constructs were transfected into COS-1 monkey kidney cells (ATCC) No. CRL1650, by standard techniques. Briefly, prior to transfection, 4–5×$10^5$ COS-1 cells in logrithmic-phase growth were plated at a density of $10^4$ cells per $cm^2$ in 100 millimeter plates. Three hours before transfection, the host cells were refed with fresh medium containing 10% (v/v) FCS. Calcium phosphate-DNA precipitates were prepared by standard procedure, see for instance Graham and Van der Eb (1973) *Virology* 52:456–457. To ensure preparation of very fine precipitates, the DNA-$CaCl_2$ and HEPES (N-2-hydroxyethylpiperazine-N'-2-ethanesulfonic acid)-buffered sodium phosphate solutions were mixed under a gentle stream of nitrogen. The precipitates were allowed to stand 30 minutes before being added to the host cells. The plasmid DNA (supercoiled, carrier-free) was employed in an amount of 10 ug per 4–5×$10^5$ COS-1 cells.

As a control, pSV1.CAT plasmid alone was also employed to transfect the COS-1 cells. In addition, the plasmid pSV2.CAT was employed to transfect the host cells, see FIG. 9E. This plasmid is similar to plasmid pSV1.CAT, but contains both 72-bp enhancer repeats of SV40, see Gorman et al., 1982, supra.

Thirty six hours after transfection, the host cells were harvested by scraping and the extracts prepared and assayed for CAT activity by thin layer chromatography. Briefly, the cell extracts were prepared by sonicating the washed, pelleted cells in 100 ul of 0.25M Tris-hydrochloride (pH 7.8). The cells were then spun for 15 minutes at 4° C. and then the supernatants were removed and assayed for CAT enzyme activity.

The assay procedure employed the following mixture (in a final volume of 180 ul): 100 ul of 0.25M Tris-hydrochloride (pH 7.5); 20 ul of cell extract; 1 uCi of [$^{14}$C] chloramphenicol (15 uCi/mmol; New England Nuclear Corp.); and, 20 ul of 4 mM acetyl coenzyme A. Control assays contained the CAT enzyme (0.01 U; P.L. Bio-Chemicals, Inc.) instead of cell extract. All of the assay reagents, except coenzyme A, were preincubated together for five minutes at 37° C. After equilibrium was reached at this temperature, the reaction was started by adding coenzyme A. After 30 minutes of incubation at 37° C., the reaction was stopped with 2 ml of cold ethyl acetate, which was also used to extract the chloramphenicol. The organic layer was dried and taken up in 30 ul of ethyl acetate, spotted on silica gel thin-layer plates, and run with chloroform methanol (95:5 ascending) followed by autoradiography of the separated acetylated chloramphenicol forms. The results of the autoradiography are reproduced in FIG. 10.

In FIG. 10, the lanes are labeled as follows: (1) control COS-cell extracts (no DNA); (2) cells transfected with plasmid pSV2.CAT (complete SV40 enhancers); (3) cells transfected with pSV1.CAT plasmid (control); (4) cells transfected with pSCR5 (Xrep at 3' end of CAT gene); (5) cells transfected with pRS23 (Xrep at 5' end of CAT gene); (6) cells transfected with pRE9 (the 750 bp enhancer-like region of Xrep at the 5' end of the CAT gene). Also in FIG. 10: "Ori-" refers to origin; "Un-" refers to unacetylated chloramphenicol; "Mono-" refers to monoacetylated forms of chloramphenicol (2 species); and, "DI-" refers to diacetylated chloramphenicol. The results of expression studies are discussed above.

EXAMPLE 7

The original Xrep clone was used as a probe to isolate and purify related sequences from the human X chromosome. Southern blot hybridization (Maniatis, supra), identified two large (10 to 20 kb) Hind III DNA fragments which cross-hybridize with Xrep. These are described in Riley et al., 1986, supra. Human genomic DNA from cell line GM6061 was Hind III digested and NaCl gradient fractionated by standard methods. Phage λ-2001 arms (Hind III) (Stratagene, Inc., San Diego, Calif.) were ligated (by methods described above) to the 10 to 25 kb NaCl gradient fraction. The recombinant phage-human DNA library thus constructed was screened with the pUCXrep1 plasmid (see FIG. 2). Two positive plaques were purified to homogeneity by four subsequent rounds of screening. The restriction enzyme maps of these clones are shown (FIG. 11). Compared to a control phage (Charon 40) lacking Xrep related sequences, the two Xrep related phage clones (designated λR1 and λR2) were both produced at 10-fold increased yield of phage DNA. Thus, as with the original Xrep sequence, λR1 and λR2 appear to positively affect yield of DNA sequences in bacteria.

The regions of the two restriction maps which are bracketed show sequences with strong homology, by cross hybridization, to the original Xrep. Thus, these sequences most likely will be useful in forming plasmid constructs designed to improve the yield of plasmid DNA and plasmid gene products.

The representative GM1416 and GM6061 cell lines are available from the Coriell Institute for Medical Research at Camden, N.J. (609/966-7377).

As will be apparent to those skilled in the art to which the invention is addressed, the present invention may be carried out by using cloning and expression vectors, host cells, culture medium, culture conditions, assays, purification techniques and sequencing techniques other than those specifically disclosed above without departing from the spirit or essential characteristics of the invention. The particular materials and processes described above are therefore to be considered in all respects as illustrative and not restrictive. The scope of the present invention is as set forth in the appended claims rather than being limited to the examples of the method and procedures set forth in the foregoing description.

The embodiments of the invention in which an exclusive property or privilege is claimed are defined as follows:

1. An isolated DNA sequence that functions to produce increased yields of cloning and expression vectors and also increased expression of an associated gene, when introduced into a host prokaryotic, yeast, or COS-1 cell, said cell not containing a restriction enzyme that cleaves said vectors, said sequence containing a functionally active portion of the DNA segment corresponding to the nucleic acid sequence shown in FIGS. 5(a), (b), and (c), joined in the order (a), (b), and (c).

2. A DNA segment according to claim 1, wherein the functionally active portion of the DNA segment includes the functionally active portion of nucleic acid numbers 1961–2170 shown in FIG. 5(c).

3. A DNA segment according to claim 1, wherein the functionally active portion of the DNA segment includes the functionally active portion of nucleic acid numbers 1–940 shown in FIGS. 5(a) and (b), joined in the order of (a) and (b).

4. A DNA segment according to claim 1, wherein the functionally active portion of the DNA segment includes the functionally active portion of nucleic acid numbers 1–750 shown in FIG. 5(a).

5. A DNA vector, containing a functionally active portion of the DNA sequence shown in FIGS. 5(a), (b), and (c), joined in the order of (a), (b), and (c), a promoter, and a cloning segment for inserting a desired gene into the vector, wherein said DNA sequence produces increased yields of the DNA vector when introduced into a host prokaryotic or eukaryotic cell.

6. The DNA vector according to claim 5, further containing a gene coding for a polypeptide inserted into the cloning segment.

7. A prokaryotic or eukaryotic host transformed by a vector of claim 6.

8. A DNA vector according to claim 5, wherein said DNA segment includes the functionally active portion of the nucleic acid sequence extending from nucleic acid number 1961 to nucleic acid number 2170 shown in FIG. 5(c).

9. A DNA vector according to claim 5, wherein the DNA segment further includes the functionally active portion of the DNA sequence extending from nucleic acid number 1 to nucleic acid number 940 shown in FIGS. 5(a) and (b), joined in the order of (a) and (b).

10. The vector according to claim 5, wherein the DNA segment includes the functionally active portion of the DNA sequence extending from nucleic acid number 1 to nucleic acid number 750 shown in FIG. 5(a).

11. A DNA sequence for increasing the transcription of an associated gene, said sequence containing active portions of the DNA segment extending from nucleic acid number 1 through nucleic acid number 940 shown in FIGS. 5(a) and (b), joined in the order of (a) and (b).

12. A DNA sequence according to claim 11, wherein the functionally active portion of the DNA segment extends from nucleic acid number 1 to nucleic acid number 750 shown in FIG. 5(a).

13. A DNA segment extending from nucleic acid number 1 to nucleic acid number 2356 shown in FIGS. 5(a), (b), and (c), joined in the order of (a), (b), and (c).

14. In a method for producing a polypeptide, including the steps of transforming a host by a DNA vector that contains an expressible gene coding for a polypeptide and isolating the polypeptide produced by said host, the improvement which is: selecting a DNA vector that includes a functionally active portion of the DNA sequence shown in FIGS. 5(a), (b), and (c), joined in the order of (a), (b), and (c), whereby said host produces an increased expression of said gene.

* * * * *

UNITED STATES PATENT AND TRADEMARK OFFICE
CERTIFICATE OF CORRECTION

PATENT NO. : 4,966,841
DATED : October 30, 1990
INVENTOR(S) : Donald E. Riley It is certified that error appears in the above-identified patent and that said Letters Patent is hereby corrected as shown below:

| Column | Line | |
|---|---|---|
| [56], the first reference under "OTHER PUBLICATIONS" | | "chromosoaml" should be --chromosomal-- |
| 2 | 19 | "SV40, virus" should be --SV40 virus,-- |
| 2 | 63 | "effective" should be --effect-- |
| 4 | 13 | "VIGS." should be -FIGS.-- |
| 5 | 36 | "SV$_{40}$" should be --SV40-- |
| 6 | 55 | "Oncce" should be --Once-- |
| 6 | 65 | "transforme" should be --transform-- |
| 7 | 62 | "table" should be --Table-- |
| 7 | 65 | "puC18" should be --pUC18-- |
| 8 | 54 | "yeat" should be --yeast-- |
| 9 | 60 | "usinng" should be --using-- |
| 10 | 40 | "sequencying" should be --sequencing-- |
| 11 | 50 | "SV$_{40}$" should be --SV40-- |
| 12 | 10 | "mallalian" should be --mammalian-- |
| 15 | 61 | "mp-phage" should be --mp19 phage-- |
| 17 | 56, 57 | "thi-ogalactopyronoside" should be --thi-ogalactopyranoside-- |
| 18 | 22 | "and" should be --an-- |

Signed and Sealed this

Thirty-first Day of March, 1992

*Attest:*

HARRY F. MANBECK, JR.

*Attesting Officer*     *Commissioner of Patents and Trademarks*